(12) United States Patent
Nishida et al.

(10) Patent No.: US 9,470,570 B2
(45) Date of Patent: Oct. 18, 2016

(54) AUTOMATIC ANALYZER AND METHOD FOR DETERMINING MALFUNCTION THEREOF

(75) Inventors: Masaharu Nishida, Tokyo (JP); Hideto Tamezane, Tokyo (JP); Isao Yamazaki, Tokyo (JP); Kumiko Kamihara, Tokyo (JP); Tomonori Mimura, Tokyo (JP)

(73) Assignee: Hitachi High-Technologies Corporation, Tokyo (JP)

(*) Notice: Subject to any disclaimer, the term of this patent is extended or adjusted under 35 U.S.C. 154(b) by 399 days.

(21) Appl. No.: 14/239,958

(22) PCT Filed: May 17, 2012

(86) PCT No.: PCT/JP2012/062675
§ 371 (c)(1),
(2), (4) Date: Mar. 10, 2014

(87) PCT Pub. No.: WO2013/042405
PCT Pub. Date: Mar. 28, 2013

(65) Prior Publication Data
US 2014/0190253 A1     Jul. 10, 2014

(30) Foreign Application Priority Data
Sep. 20, 2011    (JP) .................................. 2011-205295

(51) Int. Cl.
*G01F 23/00* (2006.01)
*G01N 35/10* (2006.01)
(Continued)

(52) U.S. Cl.
CPC ............. *G01F 23/00* (2013.01); *G01F 23/263* (2013.01); *G01L 7/00* (2013.01); *G01N 35/1011* (2013.01); *G01N 2035/009* (2013.01); *G01N 2035/1018* (2013.01); *G01N 2035/1025* (2013.01)

(58) Field of Classification Search
CPC ....... G01F 23/00; G01F 23/263; G01L 7/00; G01N 2035/009; G01N 2035/1018; G01N 2035/1025; G01N 35/1011
See application file for complete search history.

(56) References Cited

U.S. PATENT DOCUMENTS 5,319,954 A    6/1994  Koeda et al.
5,463,895 A    11/1995 Brentz
(Continued)

FOREIGN PATENT DOCUMENTS

EP    0341438 A2    11/1989
JP    05-306973 A   11/1993
(Continued)

OTHER PUBLICATIONS

International Preliminary Report on Patentability in PCT/JP2012/062675, dated Mar. 25, 2014.
(Continued)

*Primary Examiner* — Francis Gray
(74) *Attorney, Agent, or Firm* — Mattingly & Malur, PC

(57) ABSTRACT

An automatic analyzer which performs a suction operation a plurality of times on a same sample has a sample dispensing unit 9, a liquid level sensor which detects the liquid level of the sample in a sample vessel 8, an arithmetic unit 5 which computes a liquid level height h1 at the end of a first suction operation of the two consecutive suction operations from a liquid level height h0 and a sample suction volume V1 detected at the start of the first suction operation, a storage unit 7 which stores the liquid level height h1 computed by the arithmetic unit 5, and a determination unit 18 which compares a liquid level height h2 detected at the start of a second suction operation following the first suction operation with the liquid level height h1 at the end of the first suction operation.

11 Claims, 7 Drawing Sheets

(51) Int. Cl.
*G01F 23/26* (2006.01)
*G01L 7/00* (2006.01)
*G01N 35/00* (2006.01)

(56) References Cited

U.S. PATENT DOCUMENTS

| | | | |
|---|---|---|---|
| 2004/0034479 A1* | 2/2004 | Shimase | G01N 35/1016 702/19 |
| 2009/0060785 A1 | 3/2009 | Shimane et al. | |
| 2010/0313687 A1* | 12/2010 | Ogusu | B01F 11/0071 73/864.11 |
| 2011/0104810 A1 | 5/2011 | Shiba et al. | |
| 2011/0174343 A1* | 7/2011 | Azuma | G01N 35/1016 134/113 |
| 2013/0064737 A1* | 3/2013 | Mori | B01L 3/0262 422/509 |
| 2014/0220693 A1* | 8/2014 | Yamazaki | G01N 35/1016 436/54 |

FOREIGN PATENT DOCUMENTS

| | | |
|---|---|---|
| JP | 08-094642 A | 4/1996 |
| JP | 09-127136 A | 5/1997 |
| JP | 2564628 Y2 | 3/1998 |
| JP | 2003-294774 A | 10/2003 |
| JP | 2007-322285 A | 12/2007 |
| JP | 2009-058323 A | 3/2009 |
| JP | 2009-174911 A | 8/2009 |
| JP | 2010-216956 A | 9/2010 |
| WO | 92/08545 A1 | 5/1992 |

OTHER PUBLICATIONS

Extended European Search Report received in corresponding European Application No. 12833461.2 dated Mar. 25, 2015.

* cited by examiner

SUCTION VOLUME 2.0 μl

SUCTION VOLUME 3.0 μl

SUCTION VOLUME 4.0 μl

AUTOMATIC ANALYZER AND METHOD FOR DETERMINING MALFUNCTION THEREOF

TECHNICAL FIELD

The present invention relates to an automatic analyzer which executes a suction operation a plurality of times to a same sample, and a malfunction determination method of determining the presence or absence of a failure in the sample suction operation.

BACKGROUND ART

As a clinical test for analyzing the components of a biological sample such as blood or urine of a patient, there is commonly used a system that measures a change in the color of a reaction solution of a sample and a reagent as an absorbance change and performs a qualitative and quantitative analysis of target components. An automatic analyzer is used in such a clinical test. This automatic analyzer is however provided with a function of detecting a liquid surface position of the sample in a sample container with a liquid level sensor using an electrostatic capacitance during a sample dispensing operation and another function of performing a suction operation of the sample (see Patent Document 1).

PRIOR ART DOCUMENT

Patent Document

Patent Document 1: JP-2009-58323-A

SUMMARY OF THE INVENTION

Problems to be Solved by the Invention

In the clinical test, there has recently been a strong demand for the proof of validity of test results. Specifically, at present when the automation of an inspection process is widespread, it has been requested to verify whether the operation of each part of the automatic analyzer used for the test is executed correctly.

However, biological samples such as blood subjected to clinical tests in hospitals, and patients to be derived from are diverse. For example, the liquid surface state of the sample in the sample container may vary depending on the type of sample and a patient derived from. Some liquid surfaces are exposed, and some of them are coated with foam laminated. The thickness of the foam to be stacked on the liquid surface is not uniform.

When the liquid level of the sample is detected with a liquid level sensor of electrostatic capacitance type, the foam on the liquid surface is identified as the liquid surface. As a result, foam parts rather than the liquid portion of the sample can be sucked, or variations may occur in the suction rate or volume of the sample. In the suction operation of the sample, both the quality and quantity of the sample to be dispensed are required to be adequate.

An object of the present invention is to provide an automatic analyzer and a malfunction determination method thereof capable of determining whether a suction operation of a sample dispensing unit has been executed properly.

Means for Solving the Problems

In order to achieve the above object, the present invention provides an automatic analyzer that performs a suction operation a plurality of times on a same sample is equipped with a sample dispensing unit, a liquid level sensor for detecting a liquid level of the sample in a sample container, calculation means for calculating a height of a liquid level at the end of a first suction operation of the two consecutive suction operations from a height of a liquid level and a sample suction volume detected at the start of the first suction operation, storage means for storing the height of the liquid level calculated by the calculation means, and malfunction determination means for comparing a height of a liquid level detected at the start of a second suction operation following the first suction operation with the height of the liquid level at the end of the first suction operation. The automatic analyzer further determines the presence or absence of a failure in the first or second suction operation according to whether the difference between both liquid level heights exceeds a threshold value set in advance.

Effect of the Invention

According to the present invention, it is possible to determine whether the suction operation of the sample dispensing unit has been executed properly.

MODE FOR CARRYING OUT THE INVENTION

Embodiments of the present invention will hereinafter be described using the accompanying drawings.

Figure 1:
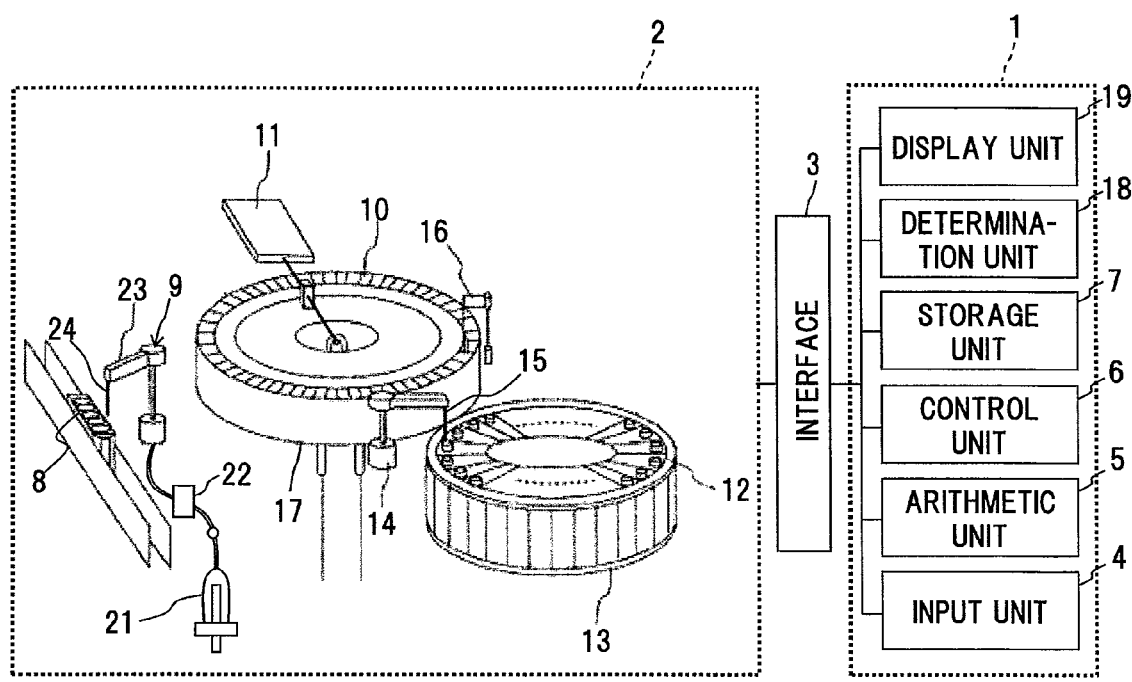
FIG. 1 is a schematic diagram showing an example of one configuration of an automatic analyzer to which the present invention is applied.

FIG. 1 is a schematic diagram showing an example of one configuration of an automatic analyzer to which the present invention is applied.

The automatic analyzer shown in FIG. 1 performs a qualitative and a quantitative analysis of a specific component of a biological sample subjected to a clinical examination. The automatic analyzer can carry out a suction operation a plurality of times on the same sample. The automatic analyzer is equipped with an analysis device 2 for executing an analysis process of the sample, and a control device 1 for controlling the operation of the analysis device 2. The analysis device 2 and the control device 1 are connected via an interface 3.

The control device 1 includes an input unit 4 for an input operation, an arithmetic unit 5 for various arithmetic processing, a control unit 6 for controlling the operation of the analysis device 2, a storage unit 7 for storing various data therein, a determination unit 18 for a malfunction determination process to be descried later, and a display unit 19 for displaying various data, an alarm, or the like to be described later.

The analysis device 2 is provided with a sample container 8, a sample dispensing unit 9 for dispensing a sample in the sample container 8, a reagent disk 13 that contains a number of reagent bottles 12 therein, a reagent dispensing unit 14 for dispensing the reagent of each reagent bottle 12, a reaction vessel 10 for mixing the sample and reagent, a thermostatic tank 17 for holding water for immersing the reaction vessel 10, a stirring mechanism 16 for stirring the sample and reagent in the reaction vessel 10, and a photometric unit 11 for measuring the absorbance of mixed liquid of the sample and reagent in the reaction vessel 10.

The sample dispensing unit 9 is furnished with a sample probe 24, a sample dispensing cylinder 21 for sucking the sample in the sample container 8 into the sample probe 24 and discharging the sample inhaled in the sample probe 24 into the reaction vessel 10, and a liquid level detection unit 23 having a liquid level sensor (not shown) for detecting the liquid level of the sample in the sample container 8. As the liquid level sensor, there can be used, for example, a type of general electrostatic capacity which detects a change in electrostatic capacitance between the sample probe 24 and the sample. Further, a pressure sensor 22 for measuring the suction pressure of the sample by the sample dispensing unit 9 is provided between the sample probe 24 and the sample dispensing cylinder 21.

The operation of the analyzer 2 is controlled by the control unit 6 of the control device 1 through the interface 3. A description will now be made of a basic operation for the measurement of the sample by the analysis device 2. The control device 1 first drives the sample dispensing unit 9 having the liquid level detection unit 23 to suck the required amount of sample into the sample probe 24 from the sample container 8. Then, the control device 1 discharges the sample sucked into the sample probe 24 into the reaction vessel 10. The control device 1 similarly drives the reagent dispensing unit 14 to suck the required amount of reagent into the probe 15 of the reagent dispensing unit 14 from the reagent bottle 12 and discharge the same into reaction vessel 10. The control device 1 next drives the stirring mechanism 16 to stir each sample in the reaction vessel 10 with the reagent. Thereafter, the absorbance of the liquid in the reaction vessel 10, i.e., the mixed liquid of sample and reagent is measured with the photometric unit 11, and data input from the photometric unit 11 is converted to a measurement result by the arithmetic unit 5. The obtained measurement result is stored in the storage unit 7 and can also be displayed on the display unit 19 as needed. Although not shown in particular, an output device such as a printer and recording means is connected to the control device, and various data may be output appropriately to a paper and a storage medium through the output device.

Figure 2:
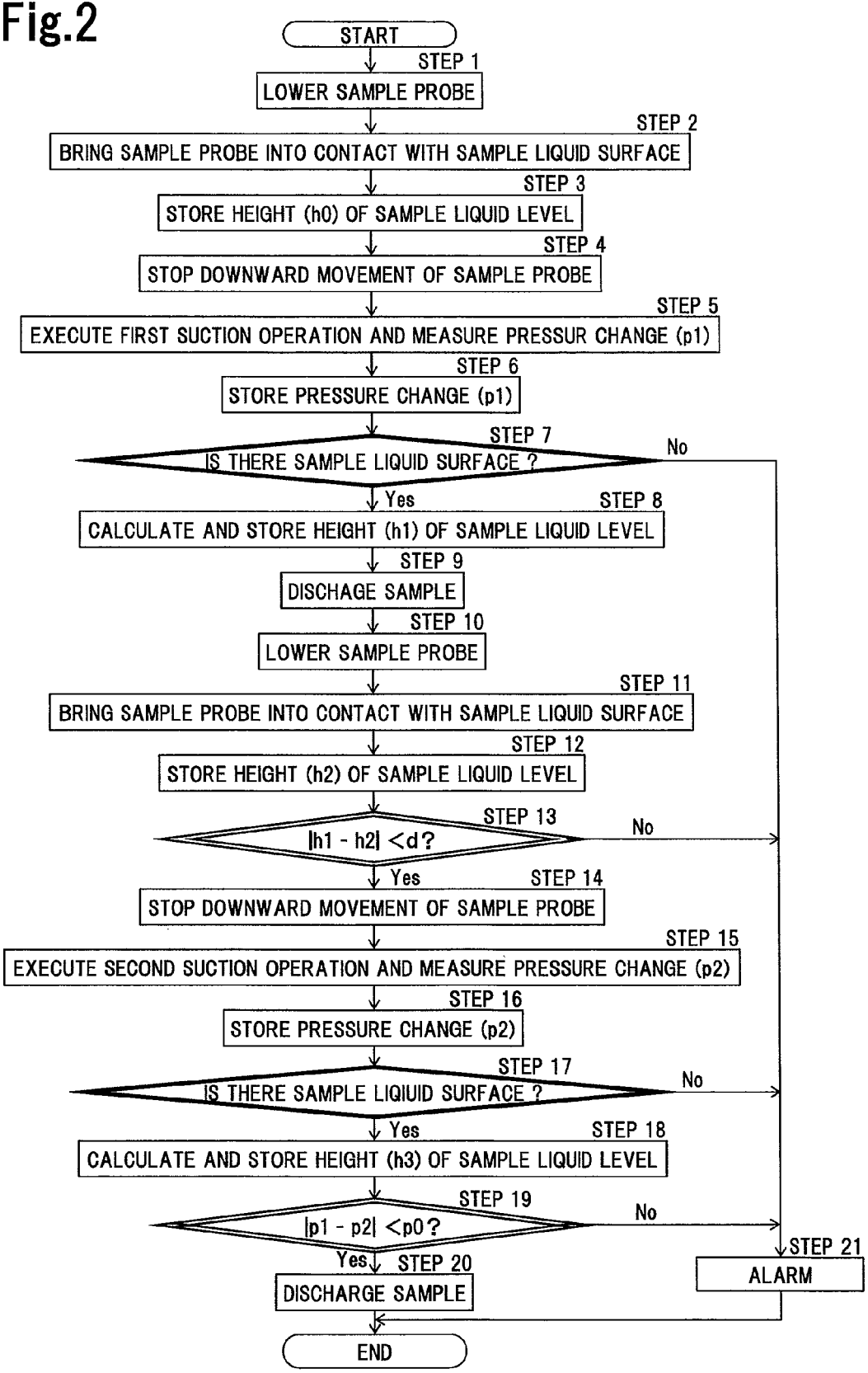
FIG. 2 is a flowchart showing an example of a control procedure for a sample suction operation of the analyzer by a control device including a malfunction determination process by malfunction determination means.

FIG. 2 is a flowchart showing one example of a control procedure for a sample suction operation of the analyzer 2 by the control device 1 including a malfunction determination process by the determination unit 18.

The flowchart of FIG. 2 represents a procedure where two items are measured with respect to the same single sample and includes a procedure for execution of a first suction operation related to the measurement of a first item and a second suction operation related to the measurement of a second item.

<Steps 1-3>

When the procedure of FIG. 2 starts, the control device 1 first drives the sample dispensing unit 9 along with the measurement of the first item to place the sample probe 24 in the sample container 8 and lower it (Step 1), thereby bringing the tip (opening) of the sample probe 24 into contact with the liquid surface or level of the sample in the sample container 8 (Step 2). It should be recognized by the detection signal from the liquid level sensor that the tip of the sample probe 24 is in contact with the liquid surface of the sample prior to the next action; the control device 1 thereafter stores in the storage unit 7 a height h0 of the liquid level of the sample recognized on the basis of the detection signal of the liquid level sensor and an operation command value to the sample dispensing unit 9 (Step 3).

<Steps 4-6>

When it is recognized by the detection signal from the liquid level sensor that the tip of the sample probe 24 has contacted the liquid surface of the sample, the control device 1 stops the downward movement of the sample probe 24 (Step 4). At this time, there is a small delay in response from both the recognition of the liquid level detection to the time when the descent stop of the sample probe 24 is commanded and the instruction to the descent stop to the time when the downward movement of the sample probe 24 actually stops. Therefore, the sample probe 24 is moved down by a minute distance after the stop command of the lowering operation (refer to a "sample probe stopping distance" in FIG. 3 and others shown below).

The control device 1 subsequently allows the sample dispensing unit 9 to execute the first suction operation of the sample (suction volume=V1) and inputs a detection signal from the pressure sensor 22 to the sample dispensing unit 9 to measure a pressure change amount p1 (see FIG. 9 below) in the first suction operation (Step 5). The control device 1 stores the measured pressure change amount p1 in the storage unit 7 (Step 6). The suction volume V1 of the sample by the first suction operation is a pre-set value with the measurement of the first item. After the operation of the sample dispensing cylinder 21 has been commanded in accordance to the configuration, the operation of the sample dispensing cylinder 21 stops to complete the first suction operation.

<Step 7>

This step is one of the malfunction determination processes described above. It is a procedure for determining whether the liquid surface of the sample is present at the end of the first suction operation (whether it is recognized on the basis of a signal from the liquid level sensor that the tip of the sample probe 24 is in contact with the liquid surface of the sample). When it has been determined in the present step that the sample probe 24 is away from the sample liquid surface, and "there is no liquid surface," the first suction operation is determined to be inappropriate. The procedure moves to Step 21 where an alarm is generated, and the procedure in the present figure is terminated. When it is determined that "the liquid surface is present" on the contrary, the procedure is transferred to the following Step 8.

Figure 10:
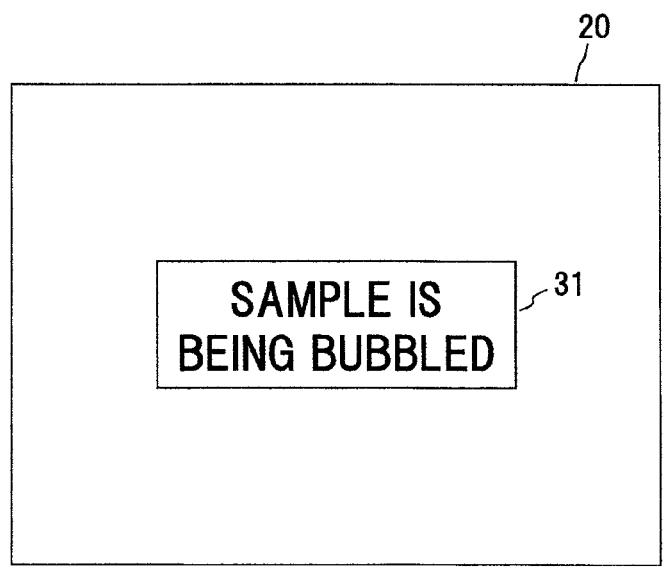
FIG. 10 is a typical diagram showing an example of a notification means for notifying it has been determined by the malfunction determination means that there is a failure in an operation.

There are two cases leading to recognition of "there is no liquid surface" in the present step; the first case is that for example there is a layer of foam on top of the sample liquid surface at the time of Step 3. The surface of the foam layer rather than the actual liquid surface is detected as the liquid surface in the same step, and the bubbles are sucked in the first suction operation. The second case is that the bubbles burst in the first suction operation in so far that a layer of foam disappears or the thickness thereof is significantly reduced. As a result of the two cases the liquid surface may not be detected at the end of the first suction operation. Since the required amount of sample cannot be sucked in the first suction operation in such a case, an alarm 31 like "sample is being foamed" and "suction operation was not done properly" is displayed on the display screen 20 of the display unit 19 as illustrated in FIG. 10 as an example. However, the alarm is intended to notify to an operator that the suction operation has not been done successfully; hence, sound, a warning sound, a warning lamp, etc. may also be applied in addition to the warning by use of such a character display.

<Steps 8-9>

If it has been determined in Step 7 that "the liquid surface is present," the control device 1 calculates the height h1 of the sample liquid level at the end of the first suction operation by the arithmetic unit 5 and stores the calculated liquid level height h1 in the storage unit 7 (Step 8). The control device 1 drives the sample dispensing unit 9 to discharge the sample sucked in the sample probe 24 in the first suction operation into the reaction vessel 10 (Step 9).

The calculation of the height h1 of the sample liquid level in Step 8 is based on the following (equation 1), for example:

$$h1 = h0 - (V1/S) \qquad \text{(equation 1)}$$

where h0, which has been read from the storage unit 7, is the height h0 (detected value) of the liquid level of the sample before the start of the first suction operation; S is the sectional area of the horizontal cross-section of the sample container 8; and V1 is the suction volume (set value) of the sample in the first suction operation.

<Steps 10-12>

The procedure subsequently goes to preparation of the sample suction operation (second suction operation) of the second item, and Steps 10-12 respectively correspond to Steps 1-3 accompanied by the first suction operation. That is, the control device 1 puts the sample probe 24 in the sample container 8 and then lowers it (Step 10). The control device 1 allows the tip of the sample probe 24 to contact the liquid surface of the sample in the sample container 8 (Step 11) and stores the recognized height h2 of sample liquid level in the storage unit 7 (Step 12).

<Step 13>

This Step 13 is also one of the malfunction determination processes mentioned above. In the present step, the determination unit 18 compares the height h1 of the sample liquid level at the end of the first suction operation and the height h2 of the sample liquid level before the start of the second suction operation with each other before the start of the second suction operation and determines whether the height h2 has not changed from the height h1. Specifically, this is a determination regarding whether the difference between the liquid level heights h1 and h2 is smaller than a threshold value d set in advance. In the present embodiment, it is decided if a condition expressed by the following (equation 2) is satisfied.

$$|h1-h2| < d \qquad \text{(equation 2)}$$

where the threshold value d may adopt, for example, the tolerance defined by the sum of a detection error specific to the liquid level sensor, and an operation error of the sample dispensing unit 9.

When there is a difference of the threshold value d or more between the liquid level heights h1 and h2, and the determination in the present step is not satisfied, it is concluded that the sample has not been normally sucked, which was caused by a malfunction in the first suction operation due to the presence of the foam layer or others on the liquid surface of the sample. The procedure then proceeds to Step 21 where such an alarm as shown in FIG. 10 is generated, and the procedure of the present diagram is terminated. On the other hand, when the difference between the liquid level heights h1 and h2 is smaller than the threshold value d, and the determination in the present step is satisfied, the processing moves to the following Step 14.

One of the cases leading to a state that does not meet the present step, for example, is that the bubbles on the sample liquid surface burst after the end of the first suction operation so that the foam layer disappears or its thickness is significantly reduced. Another example is that a bias in the distribution of the bubbles in the sample liquid surface direction on the sample liquid surface at the end of the first suction operation has changed the surface of the foam layer to be flat before the present step. The equation is given by h1>h2 in the former case; however, the expression of the latter case can be h1<h2. Thus, it is possible to analyze how the event has led to the state that the determination of Step 13 is not satisfied on the basis of information on which of the liquid level heights h1 and h2 is greater. Therefore, additional data may be notified and stored in the storage unit 7 together using the alarm 31. Such data includes which of the first and second suction operations has caused a malfunction, and what is considered to have caused the defect of the first or second suction operation from the magnitude relation of h1 and h2. These defects may be determined as; a malfunction has occurred in the second suction operation when the liquid level height h1 is large at the end of the first suction operation; or a malfunction has occurred in the second suction operation when the liquid level height h2 is large at the start of the second suction operation.

<Steps 14-16>

The following Steps 14-16 respectively correspond to Steps 4-6 accompanied with the first suction operation. That is, the control device 1 stops the downward movement of the sample probe 24 (Step 14). The control device 1 allows the sample dispensing unit 9 to execute the second suction operation (suction volume=V2) of the sample and inputs a detection signal from the pressure sensor 22 therein to thereby measure a pressure change amount p2 (see FIG. 9 and others below) in the second suction operation (Step 15). The control device 1 stores the measured pressure change amount p2 in the storage unit 7 (Step 16). The suction volume V2 of the sample by the second suction operation is a pre-set value in connection with the measurement of the second item.

<Step 17>

This Step 17 corresponds to the above Step 7 after the first suction operation. That is, the present step is also one of the malfunction determination processes described above. It is a procedure for determining whether the liquid surface of the sample is present at the end of the second suction operation (whether it is recognized on the basis of a signal from the liquid level sensor that the tip of the sample probe 24 is in contact with the liquid surface of the sample). When it is determined in the present step that the sample probe 24 is away from the sample liquid surface and "there is no liquid surface," the second suction operation is determined to be inappropriate. The procedure proceeds to Step 21 where such an alarm as shown in FIG. 10 is generated, and the processing in the present diagram is terminated. On the other hand, if it is determined that "the liquid surface is present," the procedure is transferred to the following Step 18.

One of the cases leading to recognition as "no liquid surface" in the present step is the liquid surface is not detected at the end of the second suction operation. The causes of such recognition include: the surface of the foam layer rather than the actual liquid surface being detected as the liquid surface in the same step when a layer of foam remains on top of the sample liquid surface even at the time of execution of Step 12, and the bubbles being sucked in the second suction operation; and the bubbles bursting in the second suction operation, thereby disappearing a layer of foam or reducing a thickness of the foam significantly.

<Step 18>

This Step 18 corresponds to the above Step 8 after the first suction operation. That is, the control device 1 calculates the height h3 of the sample liquid level at the end of the second suction operation by the arithmetic unit 5 and stores the calculated liquid level height h3 in the storage unit 7.

The calculation of the height h3 of the sample liquid level in the present step is based on the following (equation 3), for example:

$$h3 = h2 - (V2/S) \quad \text{(equation 3)}$$

where h2, which has been read out from the storage unit 7, is the height h2 (detected value) of the liquid level of the sample before the start of the second suction operation, S is the sectional area of the horizontal cross-section of the sample container 8, and V2 is the suction volume (set value) of the sample in the second suction operation.

<Step 19>

This Step 19 is one of the aforementioned malfunction determination processes. The present step compares the pressure change amount p1 in the first suction operation and the pressure change amount p2 in the second suction operation and determines if there is a more difference than necessary between the two. Specifically, it is determined whether the difference between the pressure change amounts p1 and p2 is smaller than a threshold value p0 set in advance, i.e., it satisfies a condition expressed by the following (equation 4):

$$|p1-p2| < p0 \quad \text{(equation 4)}$$

where the threshold value p0 may adopt, for example, the tolerance defined by the operation error or the like of the sample dispensing cylinder 21.

When there is more difference than the threshold value p0 between the pressure change amounts p1 and p2, and the determination in the present step is not satisfied, it is concluded that a malfunction occurred in the first or second suction operation due to the presence of the foam layer or others on the liquid surface of the sample, and the sample has not been normally sucked. The procedure proceeds to Step 21 where such an alarm as shown in FIG. 10 is generated and the processing of the present diagram is terminated. On the other hand, when the difference between the pressure change amounts p1 and p2 is smaller than the threshold value p0, and the determination in the present step is satisfied, the procedure moves to the following Step 20.

One of the cases leading to a state that does not meet the present step, for example, is that the bubbles on the sample liquid surface burst after the end of the first suction operation so that the foam layer disappears or its thickness is significantly reduced. Another is that a bias in the distribution of the bubbles in the sample liquid surface direction on the sample liquid surface at the end of the first suction operation has changed the surface of the foam layer to be flat before the present step. The equation is given by h1>h2 in the former case; however, the expression of the latter case can be h1<h2. Thus, it is possible to analyze how the event has led to the state that the determination of Step 13 is not satisfied from information on which of the liquid level heights h1 and h2 is greater. Therefore, the corresponding events specified from the magnitude relation of h1 and h2 can also be notified (displayed on the display unit 19, for example) or stored in the storage unit 7 along with a warning as additional information of the defective cause of the first suction operation.

The principle of the determination in Step 19 will now be described using FIG. 9 which is an explanatory diagram showing a relation between pressure and time when three types of suction operations (2.0 μL, 3.0 μL, and 4.0 μL) different in suction volume are performed on a same sample.

Figure 9:
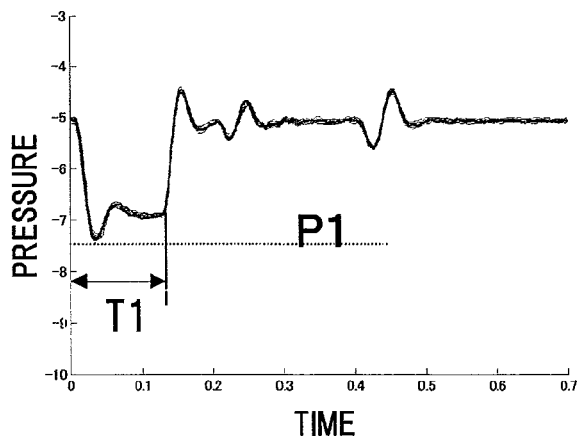
FIG. 9 is an explanatory diagram showing a relation between pressure and time when three types of suction operations different in suction volume are performed on the same sample.
Figure 9:
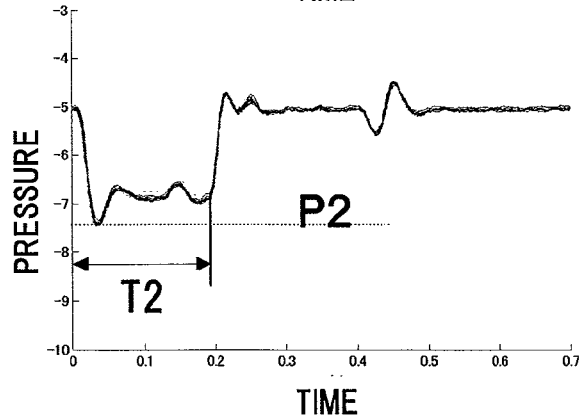
Figure 9:
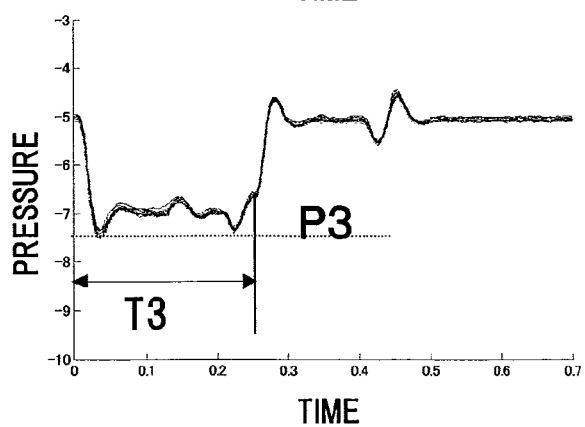

As shown in FIG. 9, pressure changes between the start of suction at a time 0 and the end of a suction operation, but it will take more time till the pressure begins to return to the pressure at the start of the suction as the suction volume becomes larger. That is, assuming that the elapsed times required until the pressure begins to return from the start of the suction in the respective suction operations at the suction volumes 2.0 μL, 3.0 μL, and 4.0 μL are T1, T2, and T, respectively, each is represented as T1<T2<T3.

On the other hand, pressure (pressure change amount, i.e., the maximum width of a change in pressure) at the lowest point of each graph is found to be substantially equal to be regardless of the volume of suction. That is, assuming that the values of the lowest points of the pressure variation lines in the respective suction operations in the suction volumes 2.0 μL, 3.0 μL, and 4.0 μL, are P1, P2 and, P3, respectively, relation of each is P1=P2=P3.

Thus, when the sample suction operation is performed plural times on the same sample as in the present embodiment, the pressure change amount becomes equal in the range of tolerance if the suction operations to be performed as targeted for the same sample are successfully executed even if the suction volume differs for every sample suction operation (even if, for example, V1>V2 in the example of FIG. 2). Thus, if a pressure change amount in some suction operation is compared with a pressure change amount in the next suction operation, and the difference between the two is within the tolerance and the condition of the above equation (4) is satisfied, both suction operations can be estimated to have been successfully executed. Reversely, when there is a difference exceeding the tolerance between the pressure change amounts in both suction operations, and the condition of the above equation (4) is not satisfied, a malfunction can be estimated to have occurred either backward or forward or in both suction operations. It is therefore possible to determine by performing the procedure in Step 19 whether there is a suction failure in at least one of the first and second suction operations.

<Step 20>

This Step 20 corresponds to the above Step 9 after the first suction operation. That is, the control device 1 drives the sample dispensing unit 9 to discharge the sample sucked into the sample probe 24 by the second suction operation into the reaction vessel 10.

When the procedure of Step 20 is completed, the control device 1 ends the procedure of FIG. 2. When there is a third item to be measured, however, the control device 1 further continues a third suction operation in accordance with the measurement recipe and executes a malfunction determination process equivalent to each of Steps 7, 13, 17, and 19 of FIG. 2 with respect to the second and third suction operations. Even if there are a fourth item and more items to be measured, the malfunction determination process equivalent to each of Steps 7, 13, 17 and 19 of FIG. 2 is similarly executed with respect to two consecutive suction operations (third and fourth suction operations or the like).

Samples such as blood subjected to clinical examinations in hospitals, and patients to be derived from are various. The liquid surface status of the sample in the sample container may also vary depending on the type of sample and the patients to be derived from. There are some liquid surfaces exposed and some covered with laminated foam. The thickness of the foam to be stacked on the liquid surface is not uniform either. First through sixth examples illustrative of the status of the sample and the behavior of the sample suction operation corresponding thereto are respectively schematically illustrated in FIGS. 3 through 8.

Figure 3:
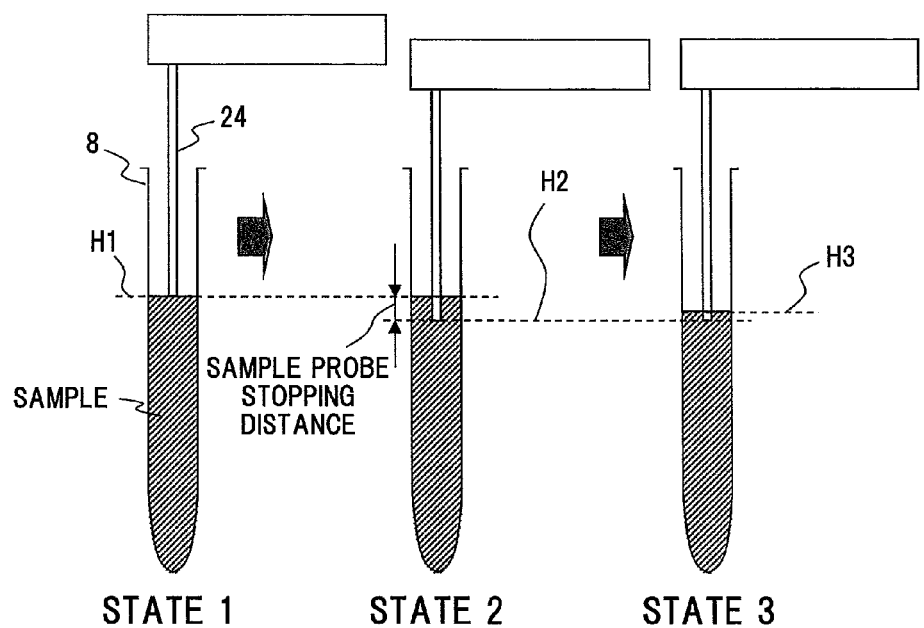
FIG. 3 is a diagram typically illustrating a first example of status of a sample and the behavior of the sample suction operation corresponding to the status.

FIG. 3 shows a state in which the sample liquid surface is exposed without a layer of foam on the sample liquid surface. The present drawing shows an example in which the state will progress like a state 1->a state 2->a state 3 accompanied with the suction operation.

In the case of the present example, since the sample liquid surface is exposed at the time prior to the suction, the liquid level height detected by the liquid level sensor in the process of lowering the sample probe 24 is a sample liquid surface (the surface of the liquid fraction of the sample) (state 1). The state 1 is equivalent to a state at the time of execution of Steps 3 and 12 in the flowchart of FIG. 2. Each of the heights h0 and h2 of the sample liquid levels detected in Steps 3 and 12 is equivalent to the height H1 of the sample liquid level before the suction, which is represented in the view of the state 1.

The downward movement of the sample probe 24 is stopped when the sample liquid surface is detected. However, the sample probe 24 is lowered by a micro distance (sample probe stopping distance) from the time when contact of the sample probe 24 with the liquid surface is detected to the time when the downward movement of the sample probe 24 is actually stopped, and is stopped with its tip being inserted into the sample by the sample probe stopping distance. As a result, the height of the tip of the sample probe 24 becomes a height H2 at the position lower than H1 (state 2). The state 2 is equivalent to a state at the time of execution of Steps 4 and 14 in the flowchart of FIG. 2.

Thereafter, when the sample suction operation started and has completed in the state 2, the sample in the sample container 8 is sucked into the sample probe 24 so that the liquid level is lowered according to the amount of suction (state 3). The state 3 is equivalent to a state after the execution of Steps 5 and 15 in the flowchart of FIG. 2. The heights h1 and h3 of the sample liquid levels calculated in Steps 8 and 18 are equivalent to a sample liquid level height H3 after the suction, which is represented in the view of the state 3. In the present example, H3 is a position higher than H2.

The suction operation of the present embodiment is ideal. There is no problem in the sample suction operation.

In the flowchart of FIG. 2, for example, when the first suction operation is executed in the state of the present embodiment, the determination in Step 7 is satisfied. Further, since there is no layer of foam on the liquid surface at the time of the state 3, the liquid level height h1 after the first suction operation calculated in Step 8 theoretically coincides with the liquid level height h2 before the second suction operation calculated in Step 12 within the range of the tolerance. Therefore, the determination in Step 13 is also satisfied. The determination in Step 17 after the second suction operation is satisfied similarly to Step 7. Further, since the first and second suction operations are both completed in the state in which the tip of the sample probe 24 has been immersed in the sample, the pressure change amounts p1 and p2 in both suction operations transit in the same manner and hence the determination in Step 19 is also satisfied. That is, the procedure of FIG. 2 can be successfully completed without issuing an alarm.

Figure 4:
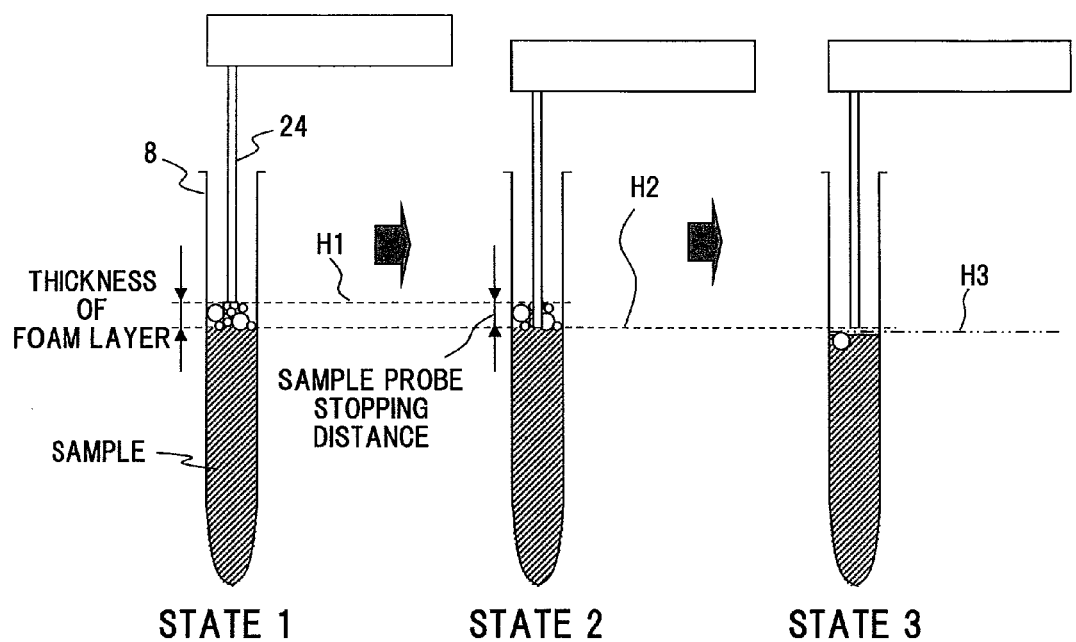
FIG. 4 is a diagram typically illustrating a second example of status of the sample and the behavior of a sample suction operation corresponding to the status.
Figure 5:
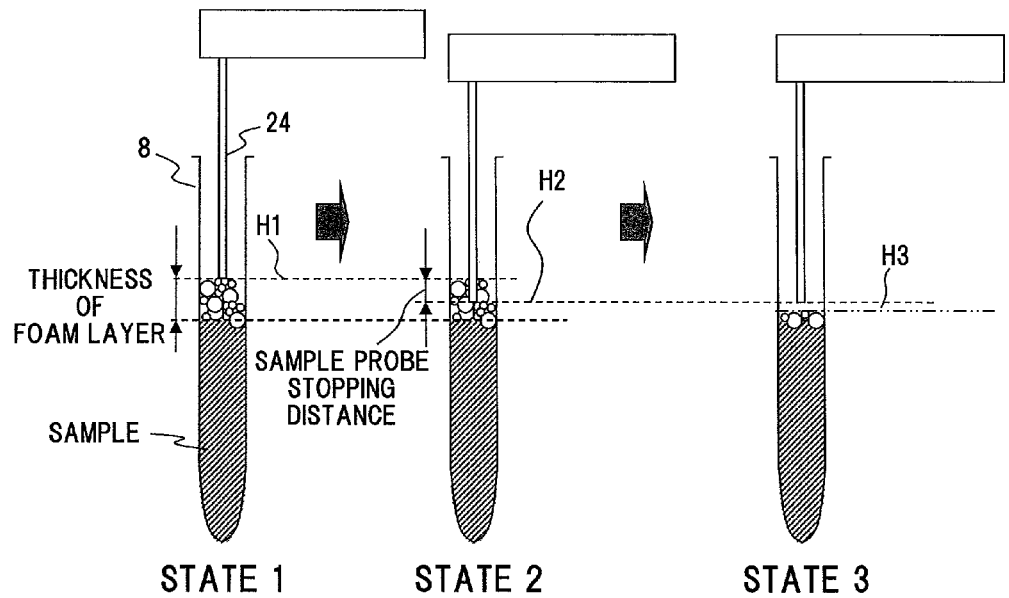
FIG. 5 is a diagram typically illustrating a third example of status of the sample and the behavior of a sample suction operation corresponding to the status.

FIGS. 4 and 5 show a state in which there is a layer of foam on the sample liquid surface and the sample liquid surface is covered with foam. Especially the example of FIG. 4 illustrates the case where the thickness of the layer of the foam is substantially equal to the sample probe stopping distance. The example of FIG. 5 illustrates the case where the thickness of the layer of the foam is greater than the sample probe stopping distance.

Since the sample liquid surface is covered with the layer of the foam at the time prior to the suction even in both examples of FIGS. 4 and 5, the height of the surface of the foam layer is detected by the liquid level sensor as the liquid level height H1 in the process of lowering the sample probe 24 (state 1). Then, in the example of FIG. 4, the actual liquid level height substantially coincides with the stop height H2 of the sample probe 24 (downward movement of the sample probe 24 stops in a state of the tip being contacted to the sample liquid surface). In the example of FIG. 5, the probe tip still does not reach the liquid surface even after the downward movement of the sample probe 24 has stopped (each state 2).

Thereafter, assume that when sample suction operation is carried out, the foam on the liquid surface and a very small amount of sample of the surface layer are sucked in the example of FIG. 4, and the majority of the foam layer is sucked in the example of FIG. 5. Alternatively, the layer of the foam is not limited to be sucked and disappears, but bubbles may burst and disappear. In any case, both in the example of FIG. 4 and the example of FIG. 5, the sample probe 24 is in contact with neither the liquid surface nor the layer of the foam after the suction operation (each state 3). In this case, as a result of mainly sucking the foam in the corresponding suction operation, it is highly probably that a required amount of sample has not been sucked both in the examples of FIG. 4 and FIG. 5.

In the flowchart of FIG. 2, for example, when the first or second suction operation is executed in the state of the example of FIG. 4 or 5, the liquid level is not detected after suction. Therefore, the determination in Step 7 or Step 17 is not satisfied, and processing is stopped with the alarm.

Figure 6:
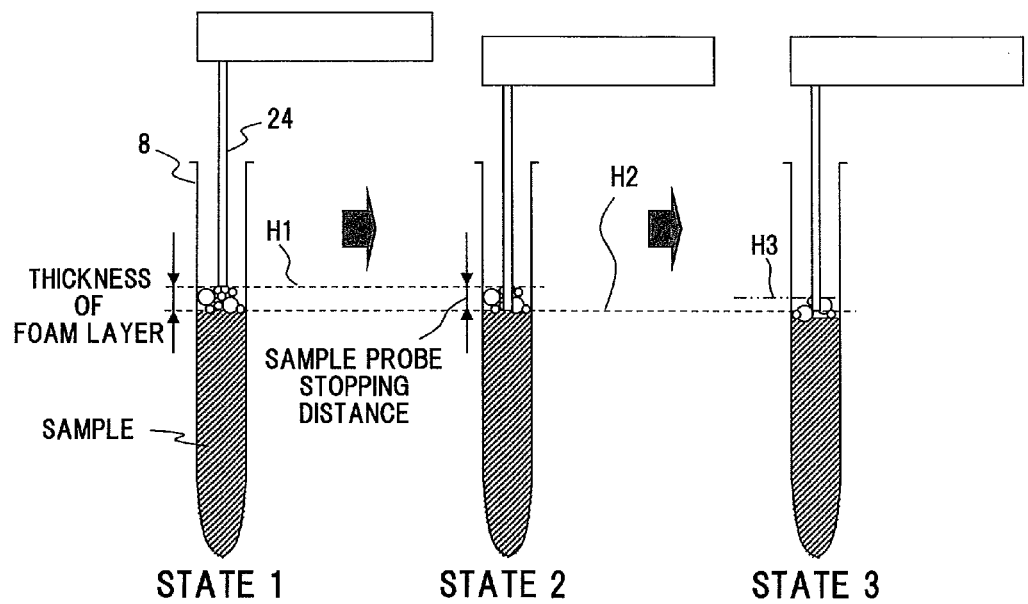
FIG. 6 is a diagram typically illustrating a fourth example of status of the sample and the behavior of a sample suction operation corresponding to the status.
Figure 7:
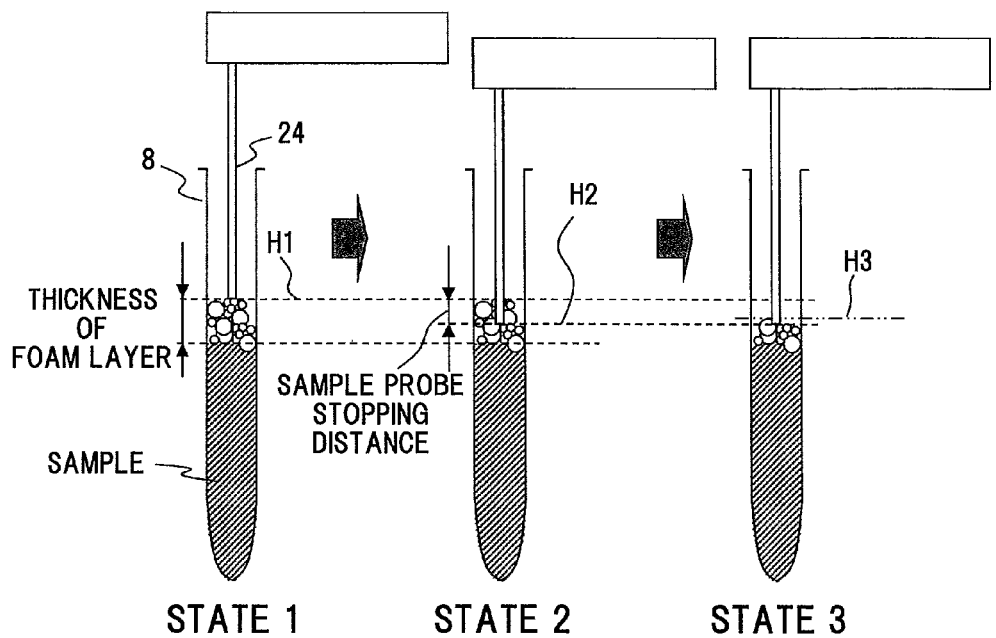
FIG. 7 is a diagram typically illustrating a fifth example of status of the sample and the behavior of a sample suction operation corresponding to the status.

FIGS. 6 and 7 show a state in which there is a layer of foam on the sample liquid surface and the sample liquid surface is covered with foam. Their states 1 and 2 are respectively the same as the states 1 and 2 in the examples of FIGS. 4 and 5.

A layer of foam still remains on the liquid surface after the suction operation in each of the examples shown in FIGS. 6 and 7. Note that the height H3 of the surface of the foam layer after the suction is still higher beyond the range of the tolerance than the height of the liquid level after the suction calculated from the liquid level height H1 (detected value) and the suction volume (set value) before the suction in the example of FIG. 6. In the example of FIG. 7, H3 substantially coincides by chance with the calculated liquid level height after the suction.

The foam is mainly sucked in a manner similar to the examples of FIGS. 4 and 5 even in the examples of FIGS. 6 and 7. Therefore, it is highly likely that a required amount of sample has not been sucked. However, if the first or second suction operation is executed in the state of the example of FIG. 4 or 5 even if the procedure of FIG. 2 is applied for example, the liquid surface is detected after the suction and hence the determination in Step 7 or Step 17 has been satisfied. It is hence not possible to recognize a suction error only by the detection of the presence or absence of the liquid level by the liquid level sensor.

In contrast, the determination in Step 7 is satisfied in the case of the present embodiment when the procedure of FIG. 2 is applied to the example of FIG. 6. However, since there is a difference exceeding the tolerance between the liquid level height after the suction calculated in Step 8 and the height H3 of the layer of foam after the actual suction, H3 is detected as the liquid level height h2 of the sample in Step 12 at the time of entering the second suction operation, and the processing of Step 13 is executed. As a result, the determination in Step 13 is not satisfied and the processing stops along with the alarm.

On the other hand, when the procedure of FIG. 2 is applied to the example of FIG. 7, the determination in Step 7 is satisfied, and the liquid level height after the suction calculated in Step 8 coincides by chance with the height H3 of the foam layer after the actual suction, so that the determination in Step 13 is also satisfied. If the state 3 of FIG. 4 or 5 is reached after the second suction operation, it is possible to recognize an error in the determination in Step 17 and stop the processing. Yet the determination in Step 17 can also be satisfied when the liquid surface is detected. When, however, foam is sucked mainly by the first suction operation, the second suction operation and the condition are not normally met inclusive of the presence or absence of the layer of foam at the beginning of suction, the thickness of the foam layer and the positional relation between the liquid surface and the probe tip. The difference usually arises beyond the error range between the pressure change amounts p1 and p2 in the first and second suction operations. Therefore, even in rare cases as shown in FIG. 7, it is possible to recognize an error in the determination in Step 19 and stop the processing.

As described above, in the present embodiment, it is possible to detect such failures in the sample suction operation as not being able to be found simply using the liquid level sensor of the electrostatic capacitance type. It is thus possible to determine whether the suction operation of the sample dispensing unit has been executed properly, that is, conclude if the sample of the proper quality has been sucked by an appropriate amount, thereby making it possible to improve the reliability of the measurement results.

The processing of both Steps 13 and 19, the example of execution of which the present embodiment has described in FIG. 2, can individually detect a failure in the sample suction operation that the liquid level sensor of the electrostatic capacitance type is not capable of simply discovering. Therefore, even if the processing of either of Steps 13 and 19 is omitted, it is still possible to improve the reliability of the measurement results as compared with the prior art.

Figure 8:
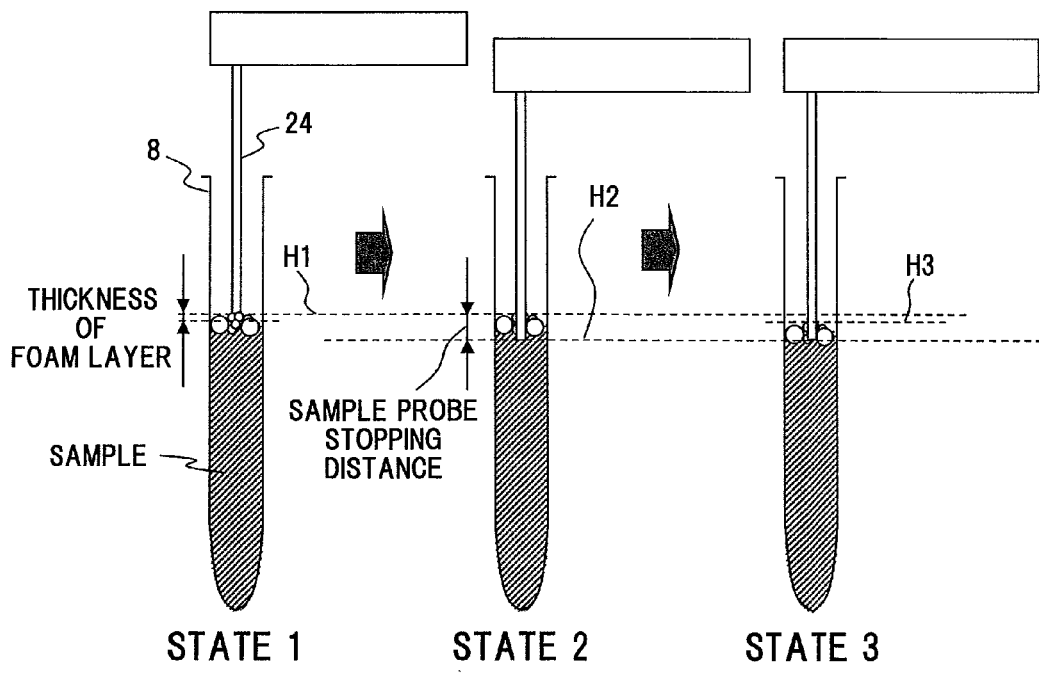
FIG. 8 is a diagram typically illustrating a sixth example of status of the sample and the behavior of a sample suction operation corresponding to the status.

There is a case where a layer of foam, by which the sample liquid surface may be covered, is thinner than a prescribed level relative to the sample probe stopping distance as shown in FIG. 8, and the height H2 of the tip of the stopped sample probe 24 assumes a position lower than the liquid surface as enough as possible to suck a required amount of sample (liquid component). In this case, even when the procedure of FIG. 2 is applied, an error possibly terminates Step 13 in the eventuality of the thickness of the foam layer being thinner beyond the tolerance, caused by bubble burst during the time between the detection of the liquid surface height before the first suction operation and the detection of the liquid surface height before the second suction operation; otherwise, the error termination is not made more than necessary.

REFERENCE NUMERALS 5 arithmetic unit (calculation means)
7 storage unit (storage means)
9 sample dispensing unit
18 determination unit (malfunction determination means)
21 sample dispensing cylinder
22 pressure sensor
23 liquid level detection unit
24 sample probe
31 alarm (a notification means)
d threshold value
h0-h3 liquid level height
V1, V2 sample suction volumes
p1, p2 pressure change amounts
p0 threshold value

The invention claimed is:

1. An automatic analyzer which performs a suction operation a plurality of times on a same sample, the automatic analyzer comprising:
    a sample dispensing unit;
    a liquid level sensor for detecting a liquid level of the sample in a sample container;
    calculation means for calculating a height of a liquid level at an end of a first suction operation of two consecutive suction operations from a height of a liquid level and a sample suction volume detected at a start of the first suction operation;
    storage means for storing the height of the liquid level calculated by the calculation means; and
    malfunction determination means for comparing a height of a liquid level detected at the start of a second suction operation following the first suction operation with the height of the liquid level at the end of the first suction operation and determining presence or absence of a failure in the first or second suction operation according to whether a difference between both liquid level heights exceeds a threshold value set in advance.

2. The automatic analyzer according to claim 1, comprising:
    a pressure sensor for measuring a suction pressure of the sample by the sample dispensing unit;
    storage means for storing a pressure change amount detected by the pressure sensor; and
    malfunction determination means for comparing pressure change amounts in the first and second suction operations and further determining the presence or absence of a failure in the first or second suction operation according to whether the difference between both pressure change amounts exceeds a pre-set threshold value when the difference between the height of the liquid level at the end of the first suction operation and the height of the liquid level at the start of the second suction operation is the threshold value or less.

3. The automatic analyzer according to claim 1, comprising notification means for notifying that there is a malfunction when it has been determined by the malfunction determination means.

4. The automatic analyzer according to claim 1, wherein when the difference between the height of the liquid level at the end of the first suction operation and the height of the liquid level at the start of the second suction operation exceeds the threshold value, the malfunction determination means determines that there is a malfunction in the first suction operation at an eventuality of the height of the liquid level at the end of the first suction operation being the larger, and determines that there is a malfunction in the second suction operation at an eventuality of the height of the liquid level at the start of the second suction operation being the larger.

5. The automatic analyzer according to claim 2, wherein the pressure sensor is disposed between a sample probe and a sample dispensing cylinder.

6. The automatic analyzer according to claim 1, wherein the liquid level sensor is an electrostatic capacitance type sensor.

7. An automatic analyzer which performs a suction operation a plurality of times on the same sample, the automatic analyzer comprising:
a sample dispensing unit;
a pressure sensor for measuring a suction pressure of the sample by the sample dispensing unit;
storage means for storing a pressure change amount detected by the pressure sensor; and
malfunction determination means for comparing pressure change amounts at the two consecutive suction operations and determining the presence or absence of a failure in the first or second suction operation according to whether the difference between both pressure change amounts exceeds a threshold value set in advance.

8. A malfunction determination method for an automatic analyzer which performs a suction operation a plurality of times on the same sample, comprising:
calculating a height of a liquid level at the end of a first suction operation of the two consecutive suction operations from a height of a liquid level and a sample suction volume detected at the start of the first suction operation; and
comparing a height of a liquid level detected at the start of a second suction operation following the first suction operation with the height of the liquid level at the end of the first suction operation and determining the presence or absence of a failure in the first or second suction operation according to whether the difference between both liquid level heights exceeds a threshold value set in advance.

9. The malfunction determination method for the automatic analyzer according to claim 8, comprising comparing pressure change amounts in the first and second suction operations and further determines the presence or absence of a failure in the first or second suction operation according to whether the difference between both pressure change amounts exceeds a threshold value set in advance when the difference between the height of the liquid level at the end of the first suction operation and the height of the liquid level at the start of the second suction operation is the threshold value or less.

10. The malfunction determination method for the automatic analyzer according to claim 8, comprising determining that there is a malfunction in the first suction operation when the height of the liquid level at the end of the first suction operation is large, and determines that there is a malfunction in the second suction operation when the height of the liquid level at the start of the second suction operation is large when the difference between the height of the liquid level at the end of the first suction operation and the height of the liquid level at the start of the second suction operation exceeds the threshold value.

11. A malfunction determination method for an automatic analyzer which performs a suction operation a plurality of times on the same sample, comprising comparing pressure change amounts at the two consecutive suction operations and determining the presence or absence of a failure in the first or second suction operation according to whether the difference between both pressure change amounts exceeds a threshold value set in advance.

* * * * *